(12) United States Patent
Harrold et al.

(10) Patent No.: US 7,378,260 B2
(45) Date of Patent: May 27, 2008

(54) PRODUCTS AND METHODS FOR REDUCING DYE ARTIFACTS

(75) Inventors: Michael P. Harrold, San Mateo, CA (US); Kevin M. Hennessy, San Mateo, CA (US); Aldrich N. K. Lau, Palo Alto, CA (US); Sean Matthew Desmond, San Carlos, CA (US)

(73) Assignee: Applera Corporation, Foster City, CA (US)

( * ) Notice: Subject to any disclaimer, the term of this patent is extended or adjusted under 35 U.S.C. 154(b) by 248 days.

(21) Appl. No.: 11/096,731

(22) Filed: Apr. 1, 2005

(65) Prior Publication Data

US 2006/0223069 A1    Oct. 5, 2006

(51) Int. Cl.
*C12P 19/34* (2006.01)

(52) U.S. Cl. .................................... 435/91.1; 435/91.2

(58) Field of Classification Search .................. None
See application file for complete search history.

(56) References Cited

U.S. PATENT DOCUMENTS

| | | | |
|---|---|---|---|
| 4,522,953 | A | 6/1985 | Barby et al. |
| 4,923,978 | A | 5/1990 | McCormick |
| 5,466,591 | A | 11/1995 | Abramson et al. |
| 5,583,162 | A | 12/1996 | Li et al. |
| 5,871,929 | A | 2/1999 | Barnes |
| 5,876,934 | A | 3/1999 | Duthie et al. |
| 6,074,827 | A | 6/2000 | Nelson et al. |
| 6,103,537 | A | 8/2000 | Ullman et al. |
| 6,197,555 | B1 | 3/2001 | Khan et al. |
| 6,228,628 | B1 | 5/2001 | Gelfand et al. |
| 6,265,193 | B1 | 7/2001 | Brandis et al. |
| 6,344,326 | B1 | 2/2002 | Nelson et al. |
| 6,365,350 | B1 | 4/2002 | Hayashizaki |
| 6,399,304 | B1 | 6/2002 | Kilger et al. |
| 6,534,269 | B2 | 3/2003 | Liu et al. |
| 6,582,987 | B2 | 6/2003 | Jun et al. |
| 6,613,525 | B2 | 9/2003 | Nelson et al. |
| 2003/0228706 | A1 | 12/2003 | Ramstad et al. |
| 2004/0016702 | A1 | 1/2004 | Henessy et al. |
| 2004/0018116 | A1 | 1/2004 | Desmond et al. |
| 2004/0018559 | A1 | 1/2004 | Lau et al. |
| 2004/0055956 | A1 | 3/2004 | Harrold |

OTHER PUBLICATIONS

Abramson, "Thermostable DNA Polymerases: An Update", In PCR Applications: Protocols for Functional Genomics, Eds. M. A. Innis, D. H. Gelfand, and J. J. Sninsky, Academic Press, 33-47 (1999).
Ignatov, et al. Mutation S543N in the Thumb Subdomain of the Taq DNA Polymerase Large Fragment Suppresses Pausing Associated with the Template Structure, *FEBS Letters,* 448, 145-148 (1999).
Ignatov, et al. "Substitution of Asn for Ser$^{543}$ in the Large Fragment of Taq DNA Polymerase Increases Efficiency of Synthesis of Long DNA Molecules", *FEBS Letters,* 425, 249-250 (1998).
Kalman, et al. "Thermostable DNA Polymerases with Altered Discrimination Properties", *Genome Science and Technology,* 1, Abstract A-14, P-42 (1995).
McCormick, "A Solid-Phase Extraction Procedure for DNA Purification", *Analytical Biochemistry,* 181, 66-74 (1989).
Mozdzanowski et al., "High yield electroblotting onto polyvinylidene difluoride membranes from polyacrylamide gels", *Electrophoresis,* 13, 59-64 (1992).
Reim et al., "Microsequence analysis of electroblotted proteins. II. Comparison of sequence performance on different types of PVDF membranes", *Anal Biochem.,* 207, 19-23 (1992).
Richards, "Ion-Exchange Membranes by Sulfonation of Poly(vinylidene Fluoride) Films", *Journal of Applied Polymer Science,* 8, 2269-2280 (1964).
Tabor, et al. "A Single Residue in DNA Polymerases of the *Escherichia coli* DNA polymerase I Family is Critical for Distinguishing Between Deoxy- and Dideoxyribonucleotides", *PNAS,* 92, 6339-6343 (1995).
Yang et al., "Sulfonation of polyvinylidene difluoride resin and its application in extraction of restriction enzymes from DNA digestion solutions", *Analytical Biochemistry,* 322, 99-103 (2003).

*Primary Examiner*—James Martinell
(74) *Attorney, Agent, or Firm*—Scott R. Bortner

(57) ABSTRACT

The present invention provides products and methods of reducing dye artifacts from chain extension reactions.

41 Claims, 13 Drawing Sheets
(13 of 13 Drawing Sheet(s) Filed in Color)

BigDye terminator v.3.1 sequencing reaction purified with
CentriSep column purification BigDye terminator v.3.1 sequencing reaction purified with
Micropure-EZ Enzyme device prior to CentriSep column purification Figure 1C - raw data
Panel 1 = CentriSep column purification
Panel 2 = Micropure-EZ Enzyme device prior to CentriSep column purification
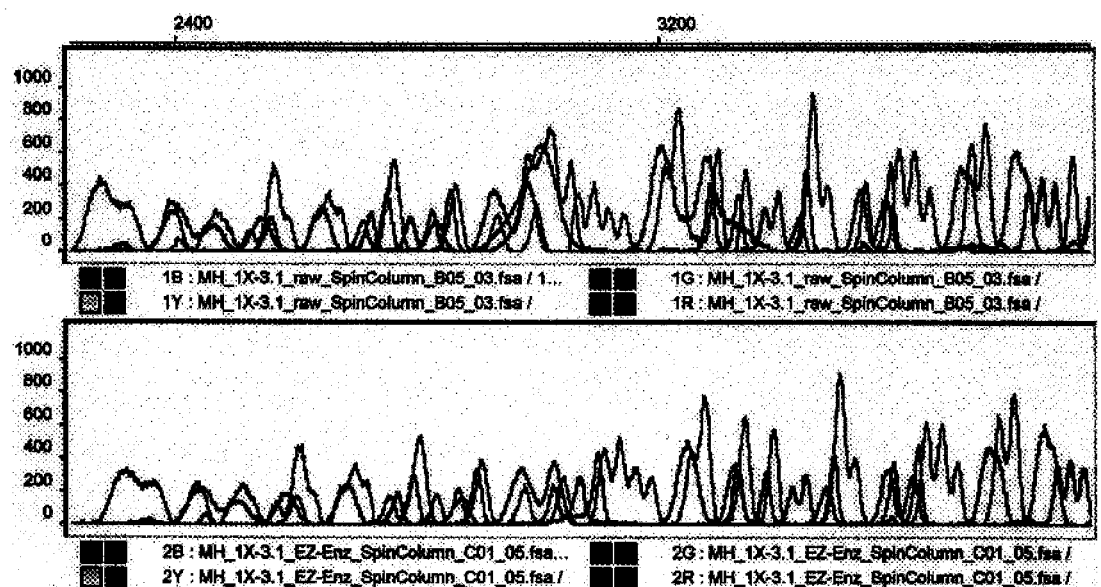

BigDye terminator v.3.1 sequencing reaction purified with SEIE purification

BigDye terminator v.3.1 sequencing reaction purified with
Micropure-EZ Enzyme device prior to SEIE purification Figure 2C - raw data
Panel 1 = SEIE purification
Panel 2 = Micropure-EZ Enzyme device prior to SEIE purification
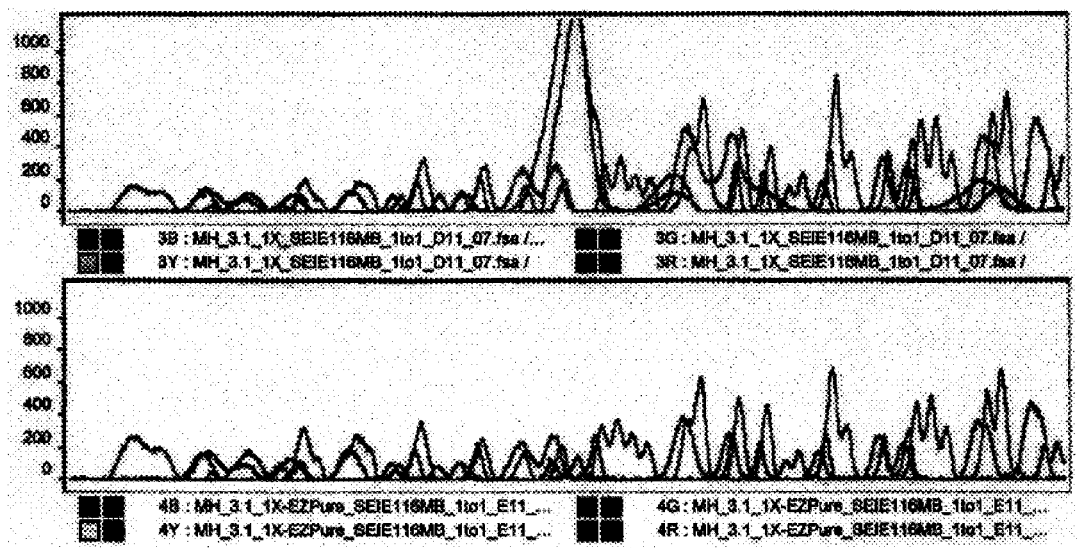

BigDye terminator v.3.1 sequencing reaction purified with CentriSep column purification BigDye terminator v.3.1 sequencing reaction purified by reaction of 20uL reaction with 50uL of HiTrap Phenyl Sepharose HP resin, followed by CentriSep column purification BigDye terminator v.3.1 reaction purified using CentriSep column with 100uL HiTrap Phenyl Sepharose HP resin mixed into the CentriSep to form a homogenous mixed bed BigDye terminator v.3.1 reaction purified using CentriSep column with 100uL HiTrap Phenyl Sepharose HP resin layered on top of the CentriSep to form a stacked bed BigDye terminator v.3.1 sequencing reaction control - no additive to reaction
CentriSep column purification BigDye terminator v.3.1 seq reaction with POROS 20HP2 HIC resin added to reaction
CentriSep column purification BigDye terminator v.3.1 seq reaction with Phenyl Sepharose 6FF resin added to reaction
CentriSep column purification

SEQUENCE LISTING

```
<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: A synthetic primer

<400> SEQUENCE: 1
caggaaacag ctatgacc                                                 18

<210> SEQ ID NO 2
<211> LENGTH: 18
<212> TYPE: DNA
<213> ORGANISM: Artificial Sequence
<220> FEATURE:
<223> OTHER INFORMATION: A synthetic primer

<400> SEQUENCE: 2
tgtaaaacga cggccagt                                                 18

<210> SEQ ID NO 3
<211> LENGTH: 516
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(516)
<223> OTHER INFORMATION: N = A, T, G or C

<400> SEQUENCE: 3
tggaggtctc cactgaaaac tctggggagg atgtgccatg gatatgggaa ggaaccctag      60
ctgattagag agcctctcgg gaggatggga ggatgggaag aggaggtttc ctgtttgtac     120
ccccgaaaat atgggtgaag gacctgtgcc gtggcccgtg agaaggaggt ctgggtgcgg     180
aaactccagg ccaggtgggt ccgggggagg ccggtcgcgc caggaaatg ccctataccg      240 cgcaggccgg accatgggaa ccccaaagcc acggatcctg ccctggctgg tgtcgcagct     300
ggacctgggg caactggagg gcgtggcctg ggtgaacaag agccgcacgc gcttccgcat     360
cccttggaag cacggcctac ggcaggatgc acagcaggag gatttcggaa tcttccaggt     420
gcgtgcgacg acctgggacg ctggaaaccc ggagctgcgc gctgggcgga aaggactcct     480
agtgggcccg gctgagaaga ctggccgtcg ttttan                              516

<210> SEQ ID NO 4
<211> LENGTH: 522
<212> TYPE: DNA
```

```
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(522)
<223> OTHER INFORMATION: N = A, T, C or G

<400> SEQUENCE: 4
tnangantgg aggtctgcac tgaagacgct ggggaaggat gtgccatgga tatgggaagg        60
aaccctagct gattagagag cctctcggga ggatgggagg atgggaagag gaggtttcct       120
ggtttgtacc cccgaaaata tgggtgaagg acctgtgccg tggcccgtga aaggaggtc        180 tgggtgcgga aactccaggc caggtgggtc cggggaggc cggtcgcgcc caggaaatgc        240
cctataacgc gcaggccgga ccatgggaac cccaaagcca cggatcctgc cctggctggt       300
gtcgcagctg gacctggggc aactggaggg cgtggcctgg gtgaacaaga gccgcacgcg       360
cttccgcatc ccttggaagc acggcctacg gcaggatgca cagcaggagg atttcggaat      420
cttccaggtg cgtgcgacga cctgggacgc tggaaacccg gagctgcgcg ctgggcggaa      480
aggactccta gtgggcccgg ctgagaagac tggccgtcgt tt                         522

<210> SEQ ID NO 5
<211> LENGTH: 514
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(514)
<223> OTHER INFORMATION: N = A, T, C or G

<400> SEQUENCE: 5
tnannantgn aggnctgcac tgaatntctg ncccaggatg tgccatggat atgggangga        60
accctagctg attagagagc ctctcgggag gatgggagga tgggaagagg aggtttcctg       120
tttgtacccc cgaaaatatg gtgaaggac ctgtgccgtg gcccgtgaga aggaggtctg       180
ggtgcggaaa ctccaggcca ggtgggtccg ggggaggccg gtcgcgccca ggaaatgccc      240
tatacgcgca ggccggacca tgggaacccc aaagccacgg atcctgccct ggctggtgtc     300
gcagctggac ctggggcaac tggagggcgt ggcctgggtg aacaagagcc gcacgcgctt    360
ccgcatccct tggaagcacg gcctacggca ggatgcacag caggaggatt tcggaatctt   420
ccaggtgcgt gcgacgacct gggacgctgg aaacccggag ctgcgctggg cggaaaggac   480
tcctagtggg cccgggctga nagactggcc cntc                                514

<210> SEQ ID NO 6
<211> LENGTH: 527
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(527)
<223> OTHER INFORMATION: N = A, T, C or G

<400> SEQUENCE: 6
tnangantgg agggtctgca ntgaagacgc tggggaagga tgtgccatgg atatgggaag        60
gaaccctagc tgattagaga gcctctcggg aggatgggag gatgggaaga ggaggtttcc      120
tgtttgtacc cccgaaaata tgggtgaagg acctgtgccg tggcccgtga aaggaggtc       180
```

```
tgggtgcgga aactccaggc caggtgggtc cggggaggc cggtcgcgcc caggaaatgc      240
cctatacgcg caggccggac catgggaacc ccaaagccac ggatcctgcc ctggctggtg      300
tcgcagctgg acctggggca actggagggc gtggcctggg tgaacaagag ccgcacgcgc      360
ttccgcatcc cttggaagca cggcctacgg caggatgcac agcaggagga tttcggaatc      420
ttccaggtgc gtgcgacgac ctgggacgct ggaaacccgg agctgcgcgc tgggcggaaa      480
ggactcctag tgggcccggc ctgagaagac tggcccgtcg tttttaca                   527
```

<210> SEQ ID NO 7
<211> LENGTH: 591
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(591)
<223> OTHER INFORMATION: N = A, T, C or G

<400> SEQUENCE: 7

```
gctcctcact gnccangatt cnctcggcca gaaaggncct gcaagagctc tgatcatttt       60
ggttctgatt ccatccttag ttcttaccca ttatctgctt acccttcctc cccacccta      120 ttaagataca aagcaaaaca aaccaaaaat acagatgagt tgcttggtag agctgcctag      180
gcctccaagg cggggcccag aggatttttt gactgaaccc cctgttgtgt tttccatatg      240
tgcttcccca gaccgcccag gtttgctgaa tgtgaagccc attgaagaca ttcaagacaa      300
cctgctacaa gccctggagc tccagctgaa gctgaaccac cctgagtcct cacagctgtt      360
tgccaagctg ctccagaaaa tgacagacct cagacagatt gtcacggaac acgtgcagct      420
actgcaggtg atcaagaaga cggagacaga catgagtctt cacccgctcc tgcaactggc      480
cgggtcgttt ttacaaannn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnn n                591
```

<210> SEQ ID NO 8
<211> LENGTH: 541
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(541)
<223> OTHER INFORMATION: N = A, T, C or G

<400> SEQUENCE: 8

```
tgacncncag attcatcctg ccagaaaag gccctgcaaa gagctctgat cattttggtt       60
ctgattccat ccttagttct tacccattat ctgcttaccc ttcctcccca cctatttaag      120
atacaaagca aacaaaacca aaatacaga tgagttgctt ggtagagctg cctaggcctc      180
caaggcgggg cccagaggat tttttgactg aaccccctgt tgtgttttcc atatgtgctt      240
ccccagaccg cccaggtttg ctgaatgtga agcccattga agacattcaa gacaacctgc      300
tacaagccct ggagctccag ctgaagctga accaccctga gtcctcacag ctgtttgcca      360
aggctgctcc agaaaatgac agacctcaga cagattgtca cggaacacgt gcagctactg      420
caggtgatca agaagacgga gacagacatg agtcttcacc cgctcctgca actggccggt      480
cgttttacaa annnnnnnnn nnnnnnnnnn nnnnnnnnnn nnnnnnnnnn nnnnnnnnnn      540
``` n                                                                        541

<210> SEQ ID NO 9
<211> LENGTH: 558
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(558)
<223> OTHER INFORMATION: N = A, T, C or G

<400> SEQUENCE: 9
tgctctngct gncccagatt catcctggcc agaaaaggcc ctgcaaagag ctctgatcat    60
tttggttctg attccatcct tagttcttac ccattatctg cttacccttc ctccccacct   120
atttaagata caaagcaaaa caaaccaaaa atacagatga gttgcttggt agagctgcct   180
aggcctccaa ggcggggccc agaggatttt tgactgaac ccctgttgt gttttccata    240 tgtgcttccc cagaccgccc aggtttgctg aatgtgaagc ccattgaaga cattcaagac   300
aacctgctac aagccctgga gctccagctg aagctgaacc accctgagtc ctcacagctg   360
tttgccaagc tgctccagaa aatgacagac ctcagacaga ttgtcacgga acacgtgcag   420
ctactgcagg tgatcaagaa gacggagaca gacatgagtc ttcacccgct cctgcaactg   480
gccggtcgtt ttacaaannn nnnnnnnnnn nnnnnnnnnn nnnnnnnnnn nnnnnnnnnn   540
nnnnnnnnnn nnnnnnnn                                                558

<210> SEQ ID NO 10
<211> LENGTH: 554
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(554)
<223> OTHER INFORMATION: N = A, T, C or G

<400> SEQUENCE: 10
tngctgannc ncanattcat cctggccaga aaggccctg caaagagctc tgatcatttt    60
ggttctgatt ccatccttag ttcttaccca ttatctgctt accttcctc cccacctatt   120 taagatacaa agcaaaacaa accaaaaata cagatgagtt gcttggtaga gctgcctagg   180
cctccaaggc ggggcccaga ggattttttg actgaacccc ctgttgtgtt ttccatatgt   240
gcttccccag accgcccagg tttgctgaat gtgaagccca ttgaagacat tcaagacaac   300 tgctacaag ccctggagct ccagctgaag ctgaaccacc ctgagtcctc acagctgttt   360
gccaagctgc tccagaaaat gacagacctc agacagattg tcacggaaca cgtgcagcta   420
ctgcaggtga tcaagaagac ggagacagac atgagtcttc acccgctcct gcaactggcc   480
ggtcgttttt acaaannnn nnnnnnnnnn nnnnnnnnnn nnnnnnnnnn nnnnnnnnnn   540
nnnnnnnnnn nnnn                                                    554

<210> SEQ ID NO 11
<211> LENGTH: 404
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature

```
<222> LOCATION: (1)...(404)
<223> OTHER INFORMATION: N = A, T, C or G

<400> SEQUENCE: 11
cgctcctata gggcgatcga ctctcccccg gggaactcta gagtcgacct gcnngcatgc      60
aagcttgagt attctatagt gtcacctaaa tagcttggcg taatcatggt catagctgtt     120
tcctgtgtga aattgttatc cgctcacaat tccacacaac atacgagccg gaagcataaa     180
gtgtaaagcc tggggtgcct aatgagtgag ctaactcaca ttaattgcgt tgcgctcact     240
gcccgctttc cagtcgggaa acctgtcgtg ccagctgcat taatgaatcg gccaacgcgc     300
ggggagaggc ggtttgcgta ttgggcgctc ttccgcttcc tcgctcactg actcgctgcg     360
ctcggtcgtt cggctgcggc gagcggtatc agctcactca aagg                     404

<210> SEQ ID NO 12
<211> LENGTH: 407
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(407)
<223> OTHER INFORMATION: N = A, T, C or G

<400> SEQUENCE: 12
ctncttnngg cgaattcgaa cctcggtccc gggatcctc tagagtcgac ctgcaggcat       60
gcaagcttga gtattctata gtgtcaccta aatagcttgg cgtaatcatg gtcatagctg    120
tttcctgtgt gaaattgtta tccgctcaca attccacaca acatacgagc cggaagcata    180
aagtgtaaag cctggggtgc ctaatgagtg agctaactca cattaattgc gttgcgctca    240
ctgcccgctt tccagtcggg aaacctgtcg tgccagctgc attaatgaat cggccaacgc    300
gcggggagag gcggtttgcg tattgggcgc tcttccgctt cctcgctcac tgactcgctg    360
cgctcggtcg ttcggctgcg gcgagcggta tcagctcact caaaggc                   407

<210> SEQ ID NO 13
<211> LENGTH: 421
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)...(421)
<223> OTHER INFORMATION: N = A, T, C or G

<400> SEQUENCE: 13
tatagggcga attcnaagct cnngtacccg gggaatcctc tagagtcgac ctgcaggcat      60
gcaagcttga gtattctata gtgtcaccta aatagcttgg cgtaatcatg gtcatagctg    120
tttcctgtgt gaaattgtta tccgctcaca attccacaca acatacgagc cggaagcata    180
aagtgtaaag cctggggtgc ctaatgagtg agctaactca cattaattgc gttgcgctca    240
ctgcccgctt tccagtcggg aaacctgtcg tgccagctgc attaatgaat cggccaacgc    300
gcggggagag gcggtttgcg tattgggcgc tcttccgctt cctcgctcac tgactcgctg    360
cgctcggtcg ttcggctgcg gcgagcggta tcagctcact caaaggcggt aatacggtta    420
t                                                                    421
```

US 7,378,260 B2

PRODUCTS AND METHODS FOR REDUCING DYE ARTIFACTS

BACKGROUND OF THE INVENTION

DNA fragments generated during sequencing reactions may be subjected to size exclusion chromatography so as to reduce the amount of dye-labeled terminators loaded into an electrophoresis device. This can reduce dye artifacts that interfere with analysis of the sequencing reaction products. However, analysis of the products of many sequencing reactions, even those that are purified by size-based separation techniques, still suffer from dye artifacts.

Accordingly, there is a need for products and methods for reducing dye artifacts in chain extension reactions, e.g., in nucleic acid sequencing reactions.

SUMMARY OF CERTAIN EMBODIMENTS OF THE INVENTION

Disclosed herein is the finding that contacting a chain extension reaction solution with a material that binds proteins, e.g., binds a DNA polymerase, will reduce dye artifacts when the products of the reaction are purified and analyzed.

Accordingly, one embodiment of the present invention provides is a method of reducing dye artifacts from a chain extension reaction, including (a) contacting a chain extension reaction solution including protein with at least one protein binding material to form a complex of the protein binding material with the protein; and (b) separating the complex from the chain extension reaction solution. In some embodiments of the invention, the protein is an enzyme, e.g., a DNA polymerase.

BRIEF DESCRIPTION OF THE FIGURES

This patent or application file contains at least one drawing executed in color. Copies of this patent or patent application publication with color drawings will be provided by the Office upon request and payment of the necessary fee.

FIG. 1C depicts raw data from FIG. 1A (upper panel) and 1B (lower panel).

FIG. 2C depicts raw data from FIG. 2A (upper panel) and 2B (lower panel).

DETAILED DESCRIPTION OF THE INVENTION

Figure 1A:
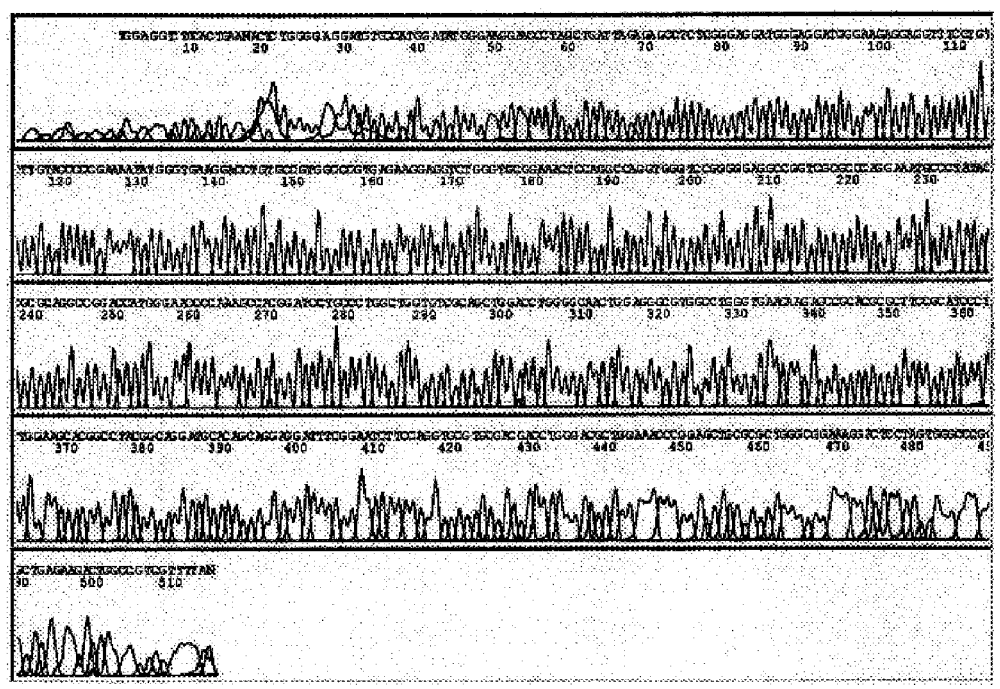
FIG. 1A depicts the results of a sequencing reaction purified with a CentriSep spin column (Princeton Separations, Adelphia, N.J., USA) The sequence listed in FIG. 1A is SEQ ID NO:3.

Disclosed herein is the finding that contacting a chain extension reaction solution with a material that binds proteins so as to create a complex of the protein-binding material with protein will reduce dye artifacts when the sample is purified so as to remove the complex and analyzed. Accordingly, in one embodiment the present invention provides a method of reducing dye artifacts from a chain extension reaction, including (a) contacting a chain extension reaction solution that includes protein with at least one protein binding material to form a complex of the protein binding material with the protein; and (b) separating the complex from the chain extension reaction solution.

In certain embodiments of the invention, the method further includes performing cycle sequencing prior to step (a). In certain embodiments of the invention, In certain embodiments of the invention, the method further includes purifying the chain extension reaction solution. In certain embodiments of the invention, the chain extension reaction solution is purified by size-based purification. In certain embodiments of the invention, the chain extension reaction solution is purified by size-based purification using a size-exclusion spin column. In certain embodiments of the invention, the chain extension reaction solution is purified by size-based purification using size-excluded ion exchange.

In certain embodiments of the invention, the method of claim 1, further includes analyzing the chain extension reaction solution on a fluorescent DNA sequencer.

In certain embodiments of the invention, the chain extension reaction solution is contacted with the protein binding material during the purification step. In certain embodiments of the invention, the chain extension reaction solution is contacted with the protein binding material prior to the purification step.

In certain embodiments of the invention, the protein is an enzyme. In certain embodiments of the invention, the enzyme is a DNA polymerase or RNA polymerase. In certain embodiments of the invention, the DNA polymerase is a thermostable DNA polymerase. In certain embodiments of the invention, the DNA polymerase is a Taq DNA polymerase. In certain embodiments of the invention, the Taq DNA polymerase is a mutated Taq DNA polymerase. In certain embodiments of the invention, the mutated Taq DNA polymerase is a mutated Taq DNA polymerase having a F667Y mutation. In certain embodiments of the invention, the protein is associated with a dye-labeled dideoxynucleotide.

In certain embodiments of the invention, the chain extension reaction is a DNA sequencing reaction. In certain embodiments of the invention, the protein binding material is a membrane. In certain embodiments of the invention, the membrane is a porous membrane. In certain embodiments of the invention, the porous membrane includes pores ranging from about 0.01 µm to about 200 µm in size. In certain embodiments of the invention, the porous membrane includes pores ranging from about 0.05 µm to about 100 µm in size. In certain embodiments of the invention, the porous membrane includes pores ranging from about 0.1 µm to about 50 µm in size. In certain embodiments of the invention, the porous membrane has a thickness ranging from about 0.1 µm to about 2000 µm. In certain embodiments of the invention, the porous membrane has a thickness ranging from about 0.5 µm to about 1500 µm. In certain embodiments of the invention, the porous membrane has a thickness ranging from about 0.5 µm to about 1000 µm.

In certain embodiments of the invention, the protein binding material is a solid support. In certain embodiments of the invention, the solid support is a microsphere. In certain embodiments of the invention, the microsphere is a polystyrene microsphere. In certain embodiments of the invention, the microsphere is a polymer microsphere having a diameter from about 100 nm to about 2000 µm. In certain embodiments of the invention, the microsphere has a diameter from about 500 nm to about 1000 µm. In certain embodiments of the invention, the microsphere has a diameter from about 1 µm to about 200 µm. In certain embodiments of the invention, the microsphere is a nonporous microsphere. In certain embodiments of the invention, the microsphere is a microporous microsphere. In certain embodiments of the invention, the microsphere is a macroporous microsphere. In certain embodiments of the invention, the microsphere is a magaporous microsphere.

In certain embodiments of the invention, the protein binding material forms a layer on the surface of a solid support. In certain embodiments of the invention, the solid support is a porous membrane. In certain embodiments of the invention, the protein binding material is associated with the solid support via covalent bonds.

In certain embodiments of the invention, the protein binding material is mixed with a size-based purification media.

In certain embodiments of the invention, the protein binding material is layered on a size-exclusion spin column.

In certain embodiments of the invention, the protein binding material is contacted with the chain extension reaction solution prior to chain extension reaction. In certain embodiments of the invention, the protein binding material remains in contact with the chain extension reaction solution during chain extension reaction.

Certain embodiments of the invention also provide a microfluidic device including a first region that includes a protein binding material capable of binding with a protein in a chain extension reaction solution.

Certain embodiments of the invention also provide a spin column including protein binding material capable of binding with a protein in a chain extension reaction solution.

In certain embodiments of the invention, proteins are removed from a solution, e.g., proteins complexed with dye-labeled nucleotides, from a solution so as to reduce the generation of dye artifacts when the solution is analyzed. The dye-labeled nucleotide is a dye-labeled nucleotide that has not been incorporated into a strand of polynucleotides during the chain extension reaction, i.e., an unincorporated dye-labeled nucleotide.

Certain embodiments of the invention provide a spin column that includes a chain extension reaction product that has been treated so as to remove unincorporated terminators.

Certain embodiments of the invention provide a spin column that includes a chain extension reaction product that has been treated so as to remove proteins.

Chain extension reactions include reactions involving the synthesis of a strand of polynucleotides, e.g., a strand of DNA. These reactions can involve a template-directed polynucleotide extension processes using at least one polymerase. Dye-labeled nucleotides and/or polynucleotides may be utilized in the chain extension reactions. Chain extension reactions include, but are not limited to, polymerase chain reactions, sequencing reactions, single base extension (SBE) reactions, mini-sequencing reactions, and the like. A chain extension reaction solution is the solution in which a chain extension reaction takes place.

A protein binding material is a material with which proteins can bind. While certain protein binding materials are exemplified herein, the invention also is meant to encompass other materials that bind with proteins so as to allow the removal of protein from a solution, e.g., from a chain extension reaction solution.

The protein present in the chain extension reaction can be any protein, e.g., any protein that one of skill in the art might add to the chain extension reaction, including proteins that are present as impurities. In some embodiments of the invention, the protein is an enzyme. In some embodiments of the invention, the enzyme is an RNA polymerase or a DNA polymerase, e.g., a Taq DNA polymerase. The Taq DNA polymerase may be a mutated Taq DNA polymerase, e.g., a Taq DNA polymerase having a F667Y mutation. The DNA polymerase may or may not be a thermostable DNA polymerase. The DNA polymerase may have a naturally occurring amino acid sequence or may be a mutant derived in part from a naturally occurring amino acid sequence.

Polymerases include, but are not limited to, the polymerases disclosed in U.S. Pat. Nos. 6,534,269; 6,399,304; 6,365,350; 6,265,193; 6,197,555; 5,876,934; 5,871,929; 5,466,591; and 6,228,628 and in Abramson, "Thermostable DNA Polymerases: An Update", In PCR Applications: Protocols for Functional Genomics, Eds. M. A. Innis, D. H. Gelfand, and J. J. Sninsky, Academic Press, 33-47 (1999); Ignatov et al., *FEBS Letters*, 448, 145-148 (1999); Ignatov et al., *FEBS Letters*, 425, 249-250 (1998); Kalman et al., "Thermostable DNA Polymerases with Altered Discrimination Properties", Genome Science and Technology, 1, Abstract A-14, P-42 (1995); and Tabor et al., *PNAS*, 92, 6339-6343 (1995). In some embodiments, the protein is a polymerase having reverse transcriptase activity. In some embodiments, the protein is a DNA dependent DNA polymerase. In some embodiments of the invention, the protein is associated with a dye-labeled dideoxynucleotide. In some embodiments of the invention, the chain extension reaction is a DNA sequencing reaction.

In some embodiments of the invention, the protein binding material is a solid support, a filter, or a membrane. In some embodiments of the invention, the protein binding material is mixed with a size-based purification media. In some embodiments of the invention, the protein-binding material is coated onto the surface of a sized-based purification medium. In some embodiments of the invention, the protein binding material is layered on a size-exclusion spin column.

In some embodiments of the invention, the method further includes performing cycle sequencing prior to contacting the chain extension reaction solution with the protein binding material. In some embodiments of the invention, the method further includes purifying the chain extension reaction solution, e.g., by size-based purification. In some embodiments of the invention, the chain extension reaction solution is purified by size-based purification using a size-exclusion spin column. In some embodiments of the invention, the chain extension reaction solution is purified by size-based purification using size-excluded ion exchange. In some embodiments of the invention, the chain extension reaction solution is contacted with the protein binding material during the size-based purification step. In some embodiments of the invention, the chain extension reaction solution is contacted with the protein binding material prior to the size-based purification step. In some embodiments of the invention, the method further includes analyzing the chain extension reaction solution on a fluorescent DNA sequencer.

Another embodiment of the invention is a kit for the purification of the sequencing reaction products. Kits of the invention may include a protein binding material and size-exclusion chromatography material. Kits of the invention may further include one or more reagents for performing a nucleic acid sequencing reaction. Such reagents include, but are not limited to a dye labeled terminators, primers, and/or DNA polymerases. The kits may also include instructions for their use for purifying sequencing reaction products.

Dye-labeled terminators may be removed from sequencing reaction products when sequencing nucleic acid sequences, such as DNA. For example, following cycle sequencing (e.g., Sanger sequencing) a purification step can be performed in an attempt to remove reaction components that could interfere with the analysis of the sequencing reaction products. In the case of cycle sequencing with dye-labeled dideoxynucleotides (i.e., dye terminators), it is helpful to remove the dye-labeled dideoxynucleotides that have not been incorporated into the DNA sequencing ladders. Failure to remove these unincorporated dye-labeled dideoxynucleotides results in artifacts in the electropherogram when the sample is analyzed on a fluorescent DNA sequencer. These artifacts, referred to herein as "dye artifacts" or simply as "artifacts", can interfere with the accurate identification of the nucleic acid sequence.

While not a limitation of the present invention, it is believed that an interaction between a dye-labeled dideoxynucleotide and a DNA polymerase used in a sequencing reaction leads to the formation of a dye artifact observed following size-based purification procedures. The polymerase is believed to form a relatively high molecular weight complex with a dye-labeled dideoxynucleotide. This complex is thought to be large enough and stable enough to pass unretained through the spin column and to elute with the DNA. However, it appears that when this complex is subjected to electrophoretic injection conditions, the complex disassociates and the dye-labeled dideoxynucleotide can be observed as a dye artifact. Based on this finding, methods and products for reducing, e.g., eliminating, dye artifacts from sequencing reactions by removing the complex prior to analysis have been developed.

The invention described herein enables the use of a microfluidic platform to perform reactions, e.g., chain extension reactions. Such platforms are known to the art worker, e.g., described in U.S. Pat. Nos. 6,613,525; 6,582,987; 6,344,326; 6,103,537; and 6,074,827. Such platforms can use size-excluded ion exchange (SEIE) as a purification method for sequencing reactions, and thus can suffer from the same problems as other size-based purifications. SEIE is described, e.g., in U.S. Patent Application Publication Numbers 20040055956; 20040018559; 20040018116; 20040016702; and 20030228706. By incorporating the methods of the present invention with the methods utilizing a microfluidic platform, these problems can be avoided.

Thus, certain embodiments of the invention provide devices, e.g., microfluidic devices, that are capable of being used to carry out a method of the invention, e.g., to remove proteins with a protein binding material, e.g., from a solution. For example, certain embodiments of the invention provide a microfluidic device having a region including a protein binding material. Certain embodiments of the invention provide a microfluidic device having a first region that includes a protein binding material and a second region for removing unincorporated nucleotide, e.g., dye-labeled terminators. The first and second regions can be connected to each other by a channel.

In some embodiments, the invention involves the use of a protein binding material that is added before, during and/or after a chain extension reaction. Such a material can bind proteins, e.g., DNA polymerases, and in doing so reduces or prevents the formation of dye artifacts when using purification methods, e.g., size-based purification methods, prior to fluorescent DNA sequencing.

It was discovered that if sequencing reaction products were reacted with an protein-binding support prior to or during a size-based purification, the dye artifacts were reduced. In some embodiments of the invention, the sequencing reaction products can be filtered through an protein-binding membrane such as the Micropure-EZ (Millipore, Billerica, Mass., USA), prior to purification using a spin column. This reduces dye artifacts in the electropherogram. (FIGS. 1A, 1B and 1C) A similar effect is seen using size-excluded ion exchange as a purification method. (FIGS. 2A, 2B, and 2C) The raw sequencing reaction products may also be purified with an affinity chromatography support such as HiTrap Phenyl Sepharose 6 (AP Biotech, Piscataway, N.J., USA) prior to purification using a spin column, and this will also reduce dye artifacts from the electropherogram. (FIGS. 3A and 3B)

Figure 4:
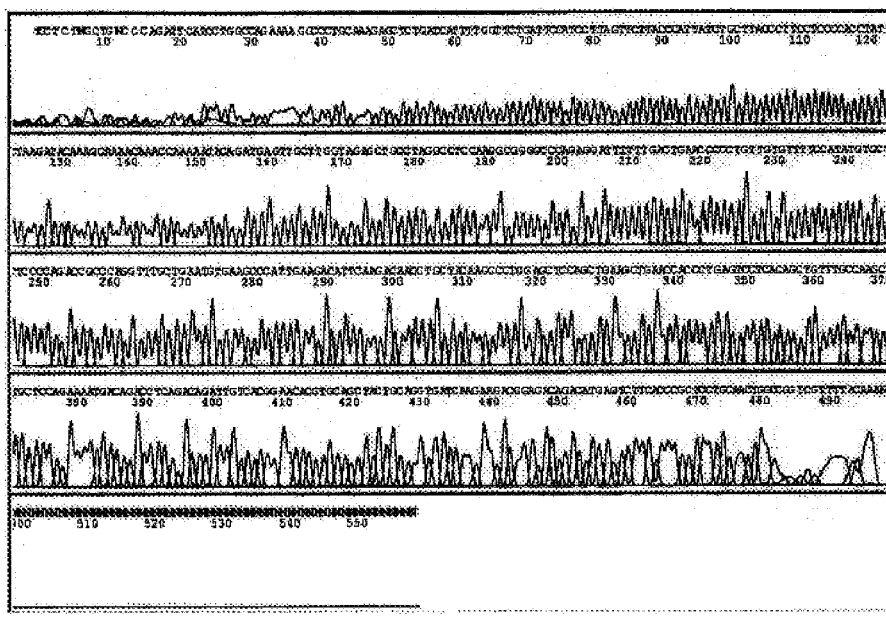
FIG. 4 depicts the results of a sequencing reaction purified using a column with a resin mixed into the column so as to form a homogenous mixed bed. The sequence listed in FIG. 4 is SEQ ID NO:9.

Another embodiment of the invention includes methods that include the step of mixing the protein binding material with size-based purification media. For example, HiTrap Phenyl Sepharose 6 can be mixed with the size-based purification media (e.g., 100 uL HiTrap Phenyl Sepharose 6 can be mixed into an 800 uL CentriSep column) to cause reduction of the dye artifacts. (FIG. 4)

Another embodiment of this invention involves coating the protein binding material onto the surface of a size-based purification medium, e.g., a porous anion exchange resin coated with multilayers of polyelectrolytes with alternative charges. (see U.S. patent application Ser. No. 10/780,963).

Figure 5:
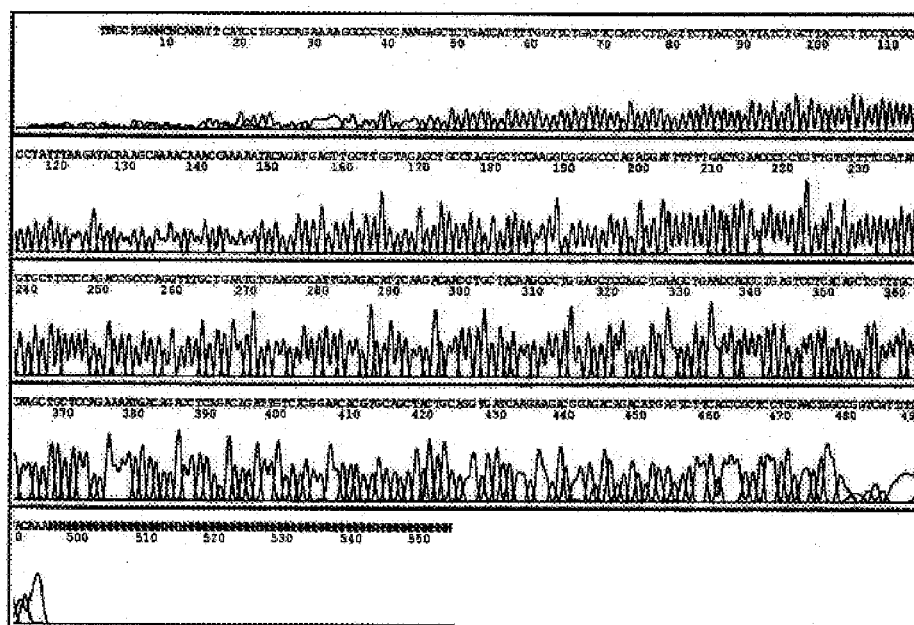
FIG. 5 depicts the results of a sequencing reaction purified using a CentriSep spin column with an protein-binding particle layered on top of the column to form a stacked bed. The sequence listed in FIG. 5 is SEQ ID NO:10.

Another embodiment of this invention involves layering the protein binding material on top of a size-exclusion spin column. For example, 100 uL HiTrap Phenyl Sepharose 6 can be pipetted onto the top of an 800 uL CentriSep column (Princeton Separations, Adelphia, N.J., USA) for reducing the dye artifacts. (FIG. 5)

These are only examples of materials (e.g. membranes and chromatography supports) that can bind proteins, e.g. DNA polymerases, and thus reduce dye artifacts from sequencing reactions. Any material that is capable of binding a protein, e.g., a material capable of binding a DNA polymerase, may also be used. These materials include, but are not limited to, POROS 20 HP2 (Applied Biosystems, Foster City, Calif., USA), HiTrap Octyl FF, HiTrap Butyl FF, HiTrap Phenyl Sepharose 6 FF-high sub, Octyl Sepharose and Butyl Sepharose (all from AP Biotech), poly(4-vinly phenol), MW 1500-7000 (Polysciences, Inc, Warrington, Pa., USA), or Isolute ENV+ (Argonaut Technologies, Foster City, Calif., USA).

Spin Columns

Spin columns, and methods for making spin columns, are known to the art worker. For example, several companies manufacture and sell spin columns, including Bio-Rad (Hercules, Calif., USA), Princeton Separations (Adelphia, N.J., USA), Amersham Pharmacia Biotech (Piscataway, N.J., USA), and Millipore Corporation (Billerica, Mass., USA). Spin columns may also be easily prepared by those of skill in the art, and many variations of procedures can be used, including, for example, filling empty columns with a size exclusion chromatography resin. Examples of useful resins for self-filled columns are Sephadex G-50 (Amersham Pharmacia Biotech, Piscataway, N.J., USA), Bio-Gel P-10 and Bio-Gel P-30 (Bio-Rad, Hercules, Calif., USA). While these products may be used in removing some unincorporated dye artifacts from DNA sequencing reactions, they suffer from residual dye artifacts when used with modern DNA sequencing kits such as BigDye Terminators v.3.1 (Applied Biosystems, Foster City, Calif., USA).

Thus, certain embodiments of the invention provide devices, e.g., spin columns, that are capable of being used to carry out a method of the invention, e.g., to remove proteins with a protein binding material, e.g., from a solution.

Solid Supports as Protein-Binding Materials

In some embodiments, this invention relates to the use of solid supports to remove proteins, e.g., DNA polymerases, from sequencing reactions, thereby reducing, if not eliminating, dye artifacts. The solid supports may be porous membranes having pore sizes ranging from about 0.01 to about 200 μm, e.g., from about 0.05 to about 100 μm, e.g., from about 0.1 to about 50 μm, and thicknesses ranging from about 0.1 to about 2000 μm, e.g., from about 0.5 to about 1500 μm, e.g., from about 0.5 to about 1000 μm. The solid supports may be polymer microspheres having particles size ranging from about 100 nm to about 2000 μm, e.g., about 500 nm to about 1000 μm; e.g., about 1 to about 200 μm. The polymer microspheres may be microporous (pore size less than about 30 Å), macroporous (pore size about 30-4000 Å), or magaporous (pore size greater than about 4000 Å, e.g., Magnapore™ prepared by Polygenetics, Los Gatos, Calif., using the high-internal-phase emulsion (HIPE) technology (see U.S. Pat. Nos. 4,522,953 and 5,583,162). In some embodiments, the pore sizes can range from about 10 Å to about 10,000 Å, e.g., from about 100 Å to about 8,000 Å. In some embodiments, the pore sizes can be greater than about 10,000 Å.

In the case of porous membranes, the analyte can be allowed to permeate (i.e., filter) through the membrane pores allowing the protein-dye terminator complex to be sequestered. In the case of polymer microspheres, the purification can be in batch or chromatography mode by exposing the analyte to a batch of polymer microspheres, or by eluting through a column of packed microspheres, respectively, allowing the protein-dye terminator complex to be sequestered. In some embodiments, surfaces may be non-porous microspheres, non-porous membranes, or other non-porous surfaces which are prepared e.g., surface functionalized, to present a protein binding surface.

Solid Supports Containing a Phenolic Moiety

One embodiment of the invention involves the removal of dye artifacts by polymer solid supports 2 containing phenolic groups on their surface, as illustrated in Scheme 1. For example, the solid support may be polymer microspheres 1 prepared by free radical polymerization of styrene and divinylbenzene, and subsequent hydroxylation. (Scheme 1) Those of ordinary skill in the art can conduct nitration/amination on 1 and subsequent diazotization/hydrolysis to prepare 2 with phenolic groups on the surface. A porogen, for example, hexanol, can be added into the monomers during emulsion polymerization to give porous polystyrene microspheres. Those of ordinary skill in the art can adjust the porosity and pore size by tailoring the porogen concentration and experimental conditions. A commercially available product with a chemical composition similar to 2 is Isolute ENV+. (Argonaut, Foster City, Calif.)

Scheme 1. Preparation of cross-linked polystyrene microspheres containing phenolic groups on the surface.

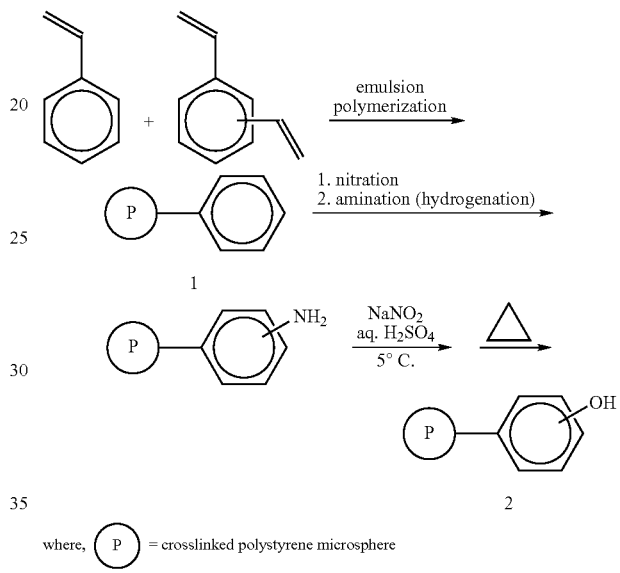

Polymer microspheres containing phenolic moiety can also be prepared by emulsion copolymerization of a hydroxystyrene precursor with at least one comonomer, which could be water-insoluble or slightly water-soluble, and a crosslinker as illustrated in Scheme 2. A porogen can also be added to tailor the porosity. In Scheme 2, the hydroxystyrene precursor is, e.g., acetoxystyrene 3 that hydrolyzes to give phenolic moiety in a subsequent step. The comonomer can be styrene; (meth)acrylamides, e.g., N-ethyl (meth)acrylamide, N-methyl (meth)acrylamide, N,N-dimethyl (meth)acrylamide, and N-butyl (meth)acrylamide; (meth)acrylates, e.g., methyl (meth)acrylate, ethyl (meth) acrylate, 2-ethylhexyl (meth)acrylate; N-vinylamides, e.g., N-methyl-N-vinyl acetamide; vinyl alkyl ethers, e.g., vinyl methyl ether and vinyl butyl ether; ally alkyl ethers, e.g., allyl ethyl ether, allyl butyl ether, and allyl benzyl ether; or a combination two or more thereof. The crosslinker includes but is not limited, e.g., to divinylbenzene, N,N'-methylenebisacrylamide, ethylene diacrylate, pentaerythritol triacrylte, or tetraethylene glycol diacrylate. Those of skill in the art can determine the appropriate amount of crosslinker to be used to prepare polymer microspheres having the desired physical and chemical properties. This phenolic polymer can also be used to fabricate porous membranes. Another protocol for the preparation of polystyrene microspheres containing phenolic moiety is reported by Jean M. J. Frechet et al., in *Polymer*, 20, 675-680 (1979).

Scheme 2. Phenolic polymer microspheres based on acetoxystyrene.

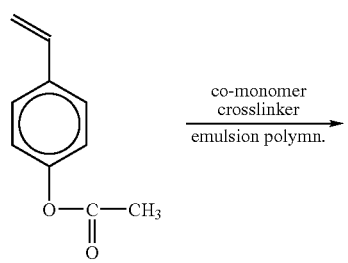

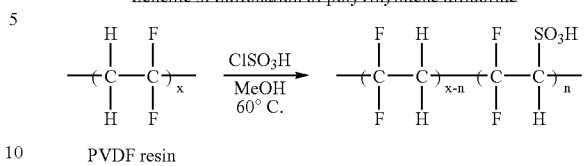

Solid Supports Based on Crosslinked Dextran and Agarose

Some embodiments of the present invention involve the use of crosslinked, alkylated or arylated dextran and agarose to bind the protein-dye terminator complex. Crosslinked dextran, includes but not limited to, Sephadex® (Scheme 4) or Sephacryl® (Scheme 5), and crosslinked agarose includes but not limited to Sepharose®. (Scheme 6)

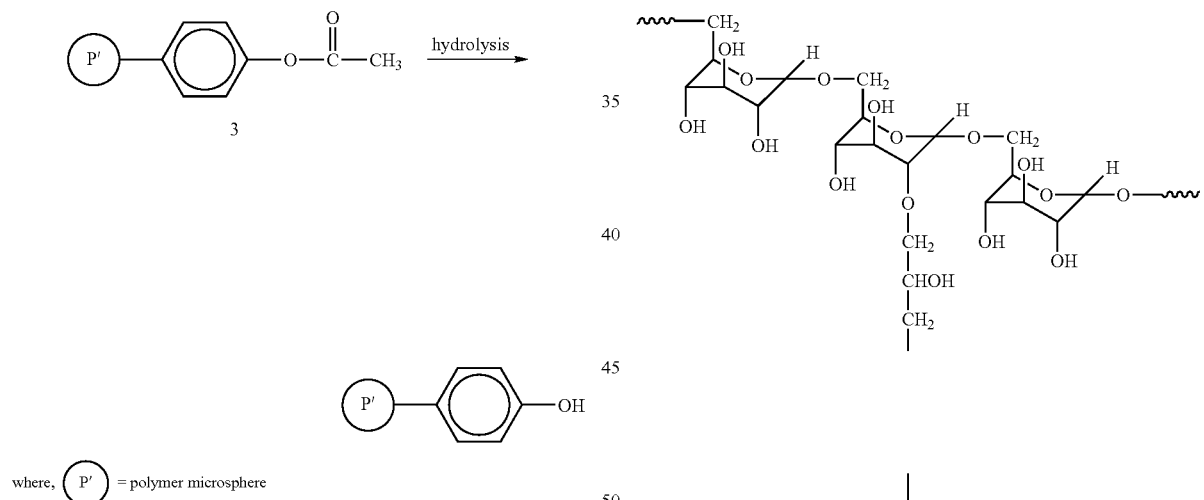

where, P' = polymer microsphere

Solid Supports Based on Polyvinylidene Difluoride (PVDF)

Another embodiment of the invention involves the use of PVDF, or its derivatives, to reduce dye artifacts by removing the protein-dye terminator complex. PVDF in particle or membrane form can be used to reduce dye artifacts. Ion-exchange membranes prepared from sulfonation of PVDF films can also be used to bind complexes of the protein binding material and the protein. (Scheme 3; Richards et al., 1964 and Yang et al., 2003) The presence of negatively charged sulfonate groups reduces passive adsorption of DNA fragments.

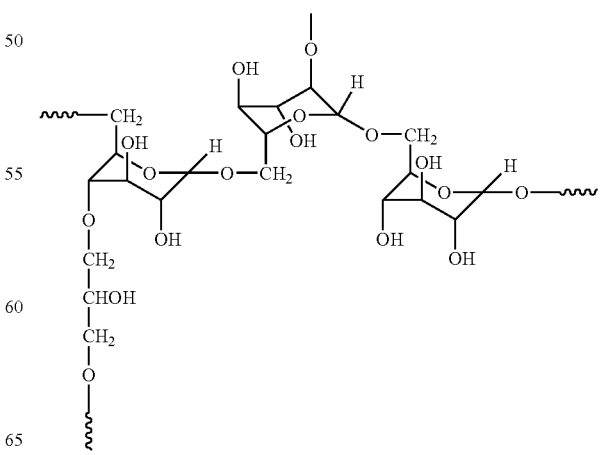

Scheme 5. Crosslinked dextran with N,N'-methylenebisacrylamide (Sephadex®)

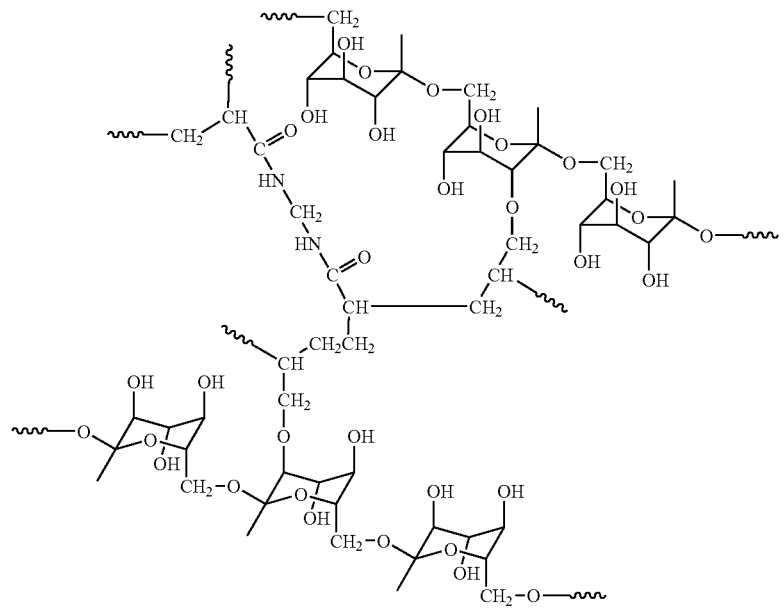

Scheme 6. Crosslinked of agarose (Sepharose ® CL)

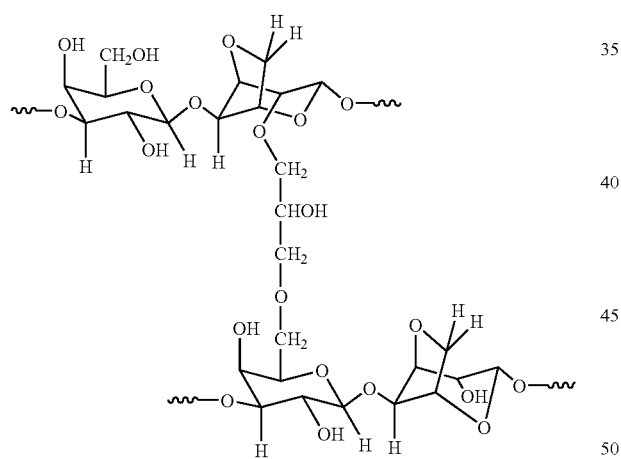

Scheme 7. Surface modification of crosslinked dextran and agarose

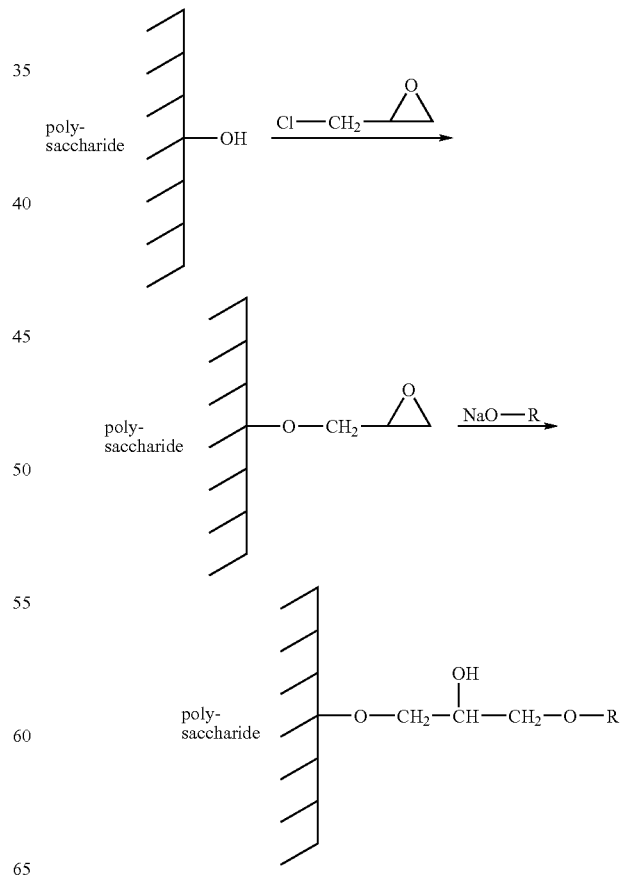

The surface hydrophilicity of rigid, highly crosslinked dextran and agarose beads or porous membranes can be tailored, for example, by introducing alkyl, aryl, or alkylaryl groups via the hydroxyl moiety. For example, a butyl or phenyl group can be covalently bonded onto the surface by reacting the surface hydroxyl groups with epichlorohydrin (see Scheme 7) and a subsequent reaction with an alkoxide or phenoxide. Due to various strength of hydrophobic interaction, proteins, peptides and enzymes will be bound to the surface. The hydrophobic groups (R in Scheme 7) on the surface bind to peptides, proteins, enzymes and protein-dye terminator complexes due to hydrophobic interaction, whereas the neutral, hydrophilic matrix minimizes passive adsorption of negatively charged DNA fragments.

Solid Supports Based on Highly Crosslinked Hydrogels

One embodiment of the invention provides for the removal of protein-dye terminator complexes with highly crosslinked hydrogels containing hydrophobic moieties on its surfaces. The hydrophobic moiety contributes to the hydrophobic interaction for binding protein-dye terminator complexes, whereas the hydrophilic matrix of the hydrogel reduces passive adsorption of DNA fragments. The hydrogel can be prepared by polymerizing a water-soluble monomer, at least one water-soluble, slightly water-soluble, or water-insoluble co-monomer, and a crosslinker. The crosslinker can be water-soluble, slightly water-soluble, or water-insoluble, e.g., N,N'-methylenebisacrylamide, tetraethyene glycol di(methy)acrylate, or pentaerythritol tri(meth)acrylate. Desired physical and chemical properties of the hydrogen can be obtained by choosing the appropriate concentration and chemical structure of the crosslinker. In various embodiments of the invention, the co-monomer includes a hydrophobic moiety, e.g., butyl (methy)acrylate, styrene, 2-ethylhexy (meth)acrylate, butyl (meth)acrylamide, N-butyl-N-vinyl formamide, N-butyl-N-vinyl-acetamide, N-phenyl-N-vinyl acetamide, vinyl methyl ether, vinyl butyl ether, allyl ethyl ether, allyl butyl ether, allyl benzyl ether, or a combination thereof. In various embodiments of the invention, the co-monomer includes an anionic moiety, e.g., acrylic acid, methacrylic acid, vinyl sulfonic acid, or styrene sulfonic acid. The anionic moiety of the hydrogel matrix can reduce passive adsorption of negatively charge DNA fragments, whereas the hydrophobic moiety can bind to protein-dye terminator complexes via hydrophobic interaction. Normal emulsion polymerization, inverse emulsion polymerization, membrane emulsification/polymerization techniques can be used to prepared hydrogel particles. Desirable particle size can be obtained by tailoring the conditions for emulsification and the use of appropriate surfactant.

In some embodiments of the invention, finished sequencing reaction products, e.g., products from a sequencing reaction following thermal cycling, can be added to a vessel containing a protein binding material prior to purification of the reaction. In some embodiments of the invention, the protein binding material can be added directly to the sequencing reaction prior to thermal cycling the reaction. The protein binding material can remain in the same vessel with the sequencing reaction while the reaction is thermal cycled.

In some embodiments of the invention, the protein binding material may be a bead or particle such as a chromatography support, or insoluble particles such as polymer microspheres. The protein binding material should be capable of binding a protein, e.g., a DNA polymerase, in the reaction buffer at room temperature, but not interfere with the reaction under the thermal cycling conditions.

The invention will now be illustrated by the following non-limiting Examples.

EXAMPLE 1

It was discovered that if sequencing reaction products were contacted with a material that binds proteins prior to or during size-based purification, dye artifacts were not observed when the products were analyzed.

DNA Sequencing Reactions 20 uL sequencing reactions were performed using 8 uL of BigDye terminator (BDT) v.3.1 ready reaction mix for each 20 uL reaction. The sequencing primer was 3.2 pmol of M13 reverse primer per reaction. (5'-CAGGAAACAGCTAT-GACC-3'; SEQ ID NO:1) The template was a PCR product with universal M13 priming sites.

Approximately 150 ng of the template was used per 20 uL reaction. The reactions were cycled in a GeneAmp 9700 (Applied Biosystems, Foster City, Calif., UA) using default sequencing conditions (96° C. for 10 seconds, 50° C. for 5 seconds, 60° C. for 240 seconds; 25 times) and pooled. The PCR product that was sequenced in FIGS. 1 and 2 was different than for FIGS. 3, 4, and 5. Varying the PCR product for sequencing had no effect on the ability to purify the sample to reduce the artifacts.

Figure 1B:
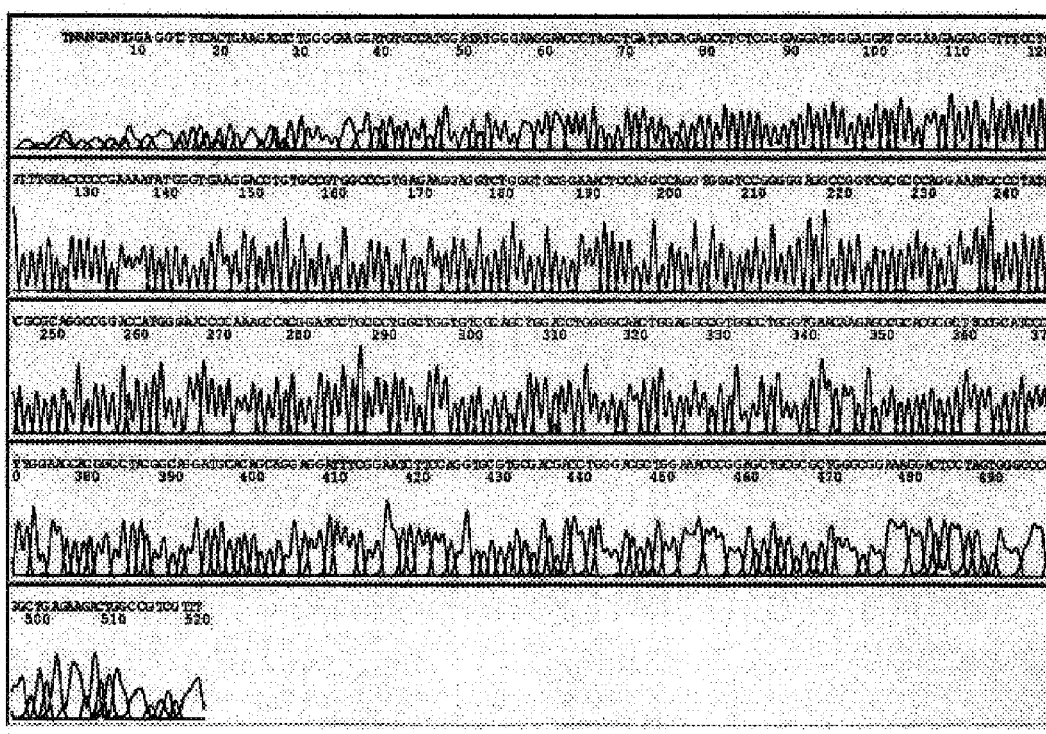
FIG. 1B depicts the results of a sequencing reaction purified with a Micropure-EZ Enzyme device (Millipore, Billerica, Mass., USA) prior to CentriSep spin column purification. The sequence listed in FIG. 1B is SEQ ID NO:4.

FIG. 1A depicts the results of a BigDye terminator version 3.1 sequencing reaction purified with CentriSep column purification. FIG. 1B depicts the results of a BigDye terminator version 3.1 sequencing reaction purified with a Micropure-EZ Enzyme device prior to CentriSep column purification. FIG. 1C depicts raw data from FIG. 1A (upper panel) and 1B (lower panel).

Figure 2A:
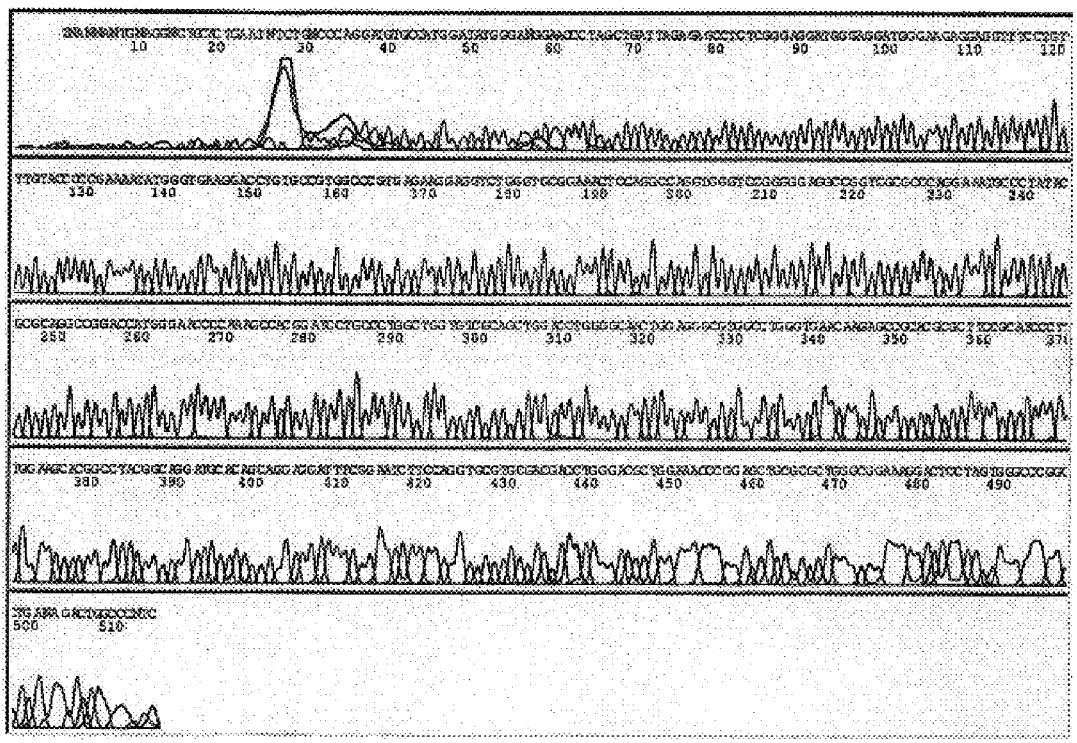
FIG. 2A depicts the results of a sequencing reaction purified with size-excluded ion exchange (SEIE) purification. The sequence listed in FIG. 2A is SEQ ID NO:5.
Figure 2B:
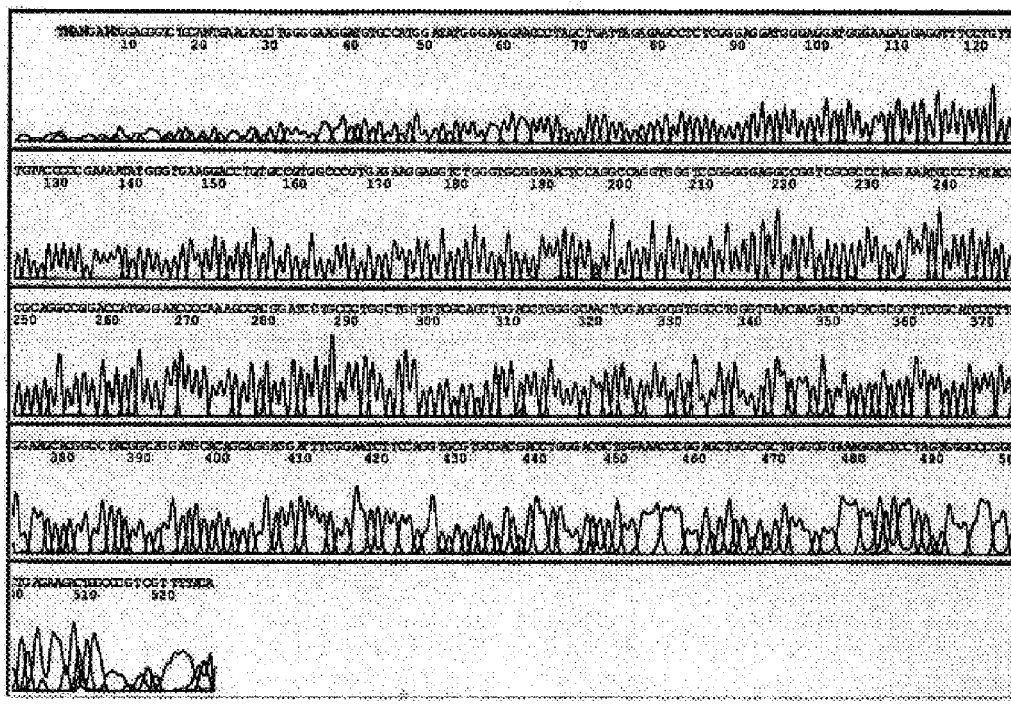
FIG. 2B depicts the results of a sequencing reaction purified with a Micropure-EZ Enzyme device prior to SEIE purification. The sequence listed in FIG. 2B is SEQ ID NO:6.
Figure 3A:
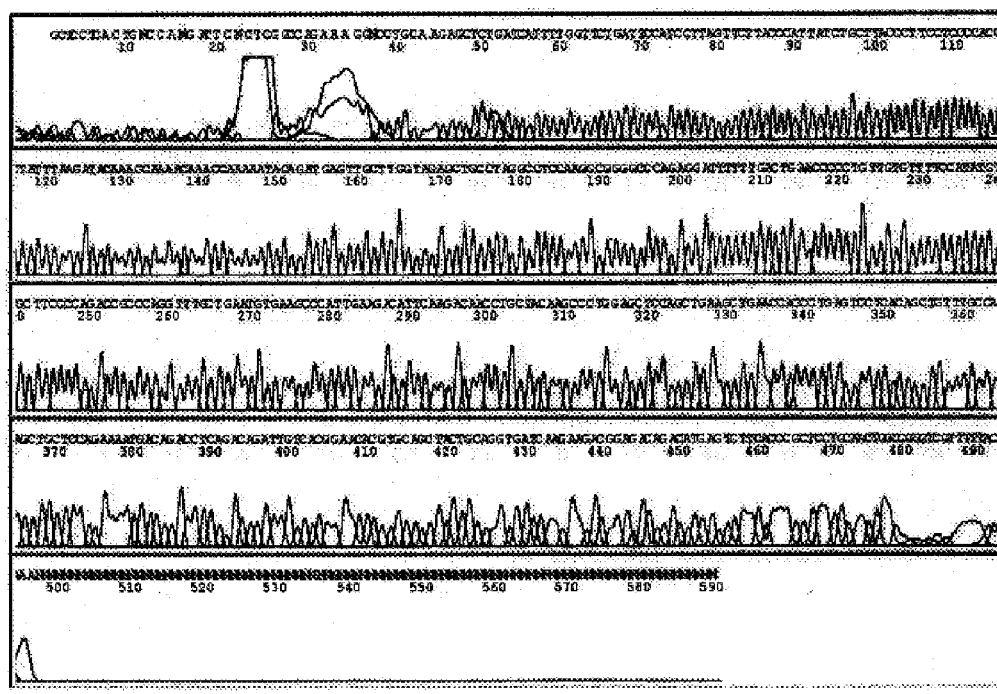
FIG. 3A depicts the results of a sequencing reaction purified using a CentriSep spin column. The sequence listed in FIG. 3A is SEQ ID NO:7.
Figure 3B:
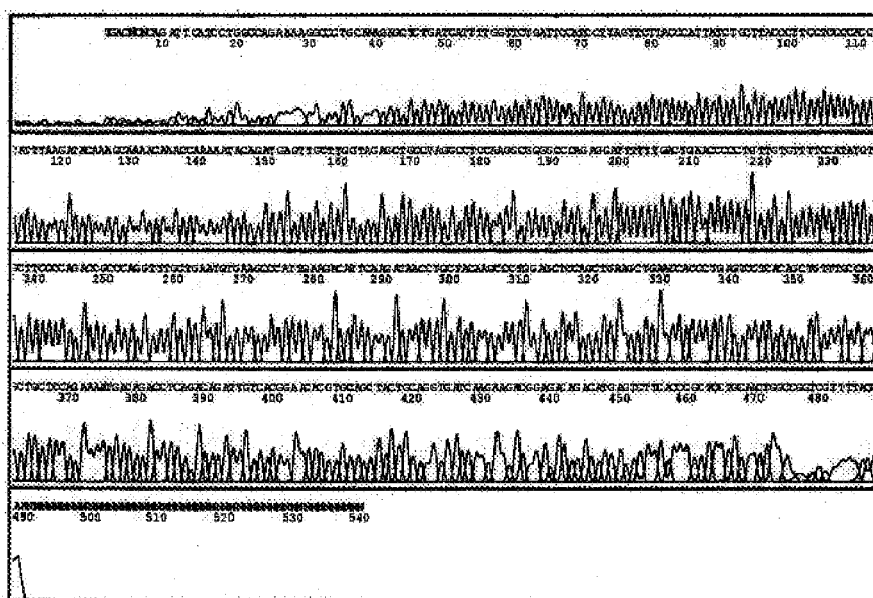
FIG. 3B depicts the results of a sequencing reaction contacted with a protein-binding particle prior to purification using a CentriSep spin column. The sequence listed in FIG. 3B is SEQ ID NO:8.

FIG. 2A depicts the results of a BigDye terminator version 3.1 sequencing reaction purified with SEIE purification. FIG. 2B depicts the results of a BigDye terminator version 3.1 sequencing reaction purified with a Micropure-EZ Enzyme device prior to SEIE purification. FIG. 2C depicts raw data from FIG. 2A (upper panel) and 2B (lower panel).

FIG. 3A depicts the results of a BigDye terminator version 3.1 sequencing reaction purified with CentriSep column purification. FIG. 3B depicts the results of a BigDye terminator version 3.1 sequencing reaction purified by reaction of 20 μL reaction with 50 μL of HiTrap Phenyl Sepharose HP resin, followed by CentriSep column purification.

FIG. 4 depicts the results of a BigDye terminator version 3.1 sequencing reaction purified using a CentriSep column with 100 μL HiTrap Phenyl Sepharose HP resin mixed into the CentriSep to form a homogenous mixed bed.

FIG. 5 depicts the results of a BigDye terminator version 3.1 sequencing reaction purified using a CentriSep column with 100 μL HiTrap Phenyl Sepharose HP resin layered on top of the CentriSep to form a stacked bed.

Enzyme Removal

An aliquot of 50 uL of pooled sequencing reaction products was added to the Micropure-EZ Enzyme device and spun at 13,000×g on a bench top centrifuge for 30 seconds. The liquid that passed through the membrane was then purified with either CentriSep or SEIE. In the case of purification using HiTrap resin prior to CentriSep columns (FIG. 3B), an aliquot of 25 uL of sequencing reaction products was mixed with 5 uL of HiTrap resin slurry and vortexed 5 minutes. The mixture was spun down, and 20 uL supernatant was pulled and loaded onto a CentriSep column.

CentriSep Purification

CentriSep columns from Princeton Separations were hydrated with 800 uL of high purity deionized water for 2 hours. An aliquot of 20 uL of sequencing reaction products was eluted through the columns. The purified samples were transferred to the ABI 3100 for analysis.

Mixed Affinity/CentriSep Columns

A CentriSep column was hydrated with 800 uL of water and vortexed. The column was allowed to stand for 30 minutes. An aliquot of 100 uL HiTrap resin slurry was added with a pipette and was vortexed. Other affinity resins can also be used. The column was then processed per the instruction included with the CentriSep columns.

Layered Affinity/CentriSep Columns

A CentriSep column was hydrated with 800 uL of water and vortexed. The column was allowed to stand for 30 minutes. Following the 30 minutes hydration, the spin column was uncapped and allowed to drain by gravity for about 10 minutes. An aliquot of 100 uL HiTrap resin slurry was carefully pipetted onto the top of the CentriSep resin bed. (Other affinity resins may also be used.) The column was then processed as per the instruction included with the CentriSep columns.

Size-Excluded Ion Exchange Purification

An aliquot of 1 uL of slurry (see 20040018559A1; 20040016702A1; and U.S. patent application Ser. No. 10/780,963 for a full description of this material) was transferred to a MicroAmp tube. An aliquot of 1 uL of sample was added, and the mixture was pipette-mixed, then vortexed for 1 minute. To the mixture, 6 uL of deionized water was added, vortexed, the resin spun down to the bottom of the tube, and the supernatant transferred to the ABI 3100 for analysis.

Electrophoresis Conditions

Electrophoresis was run on an ABI 3100 with a 36 cm capillary array, POP-6 polymer and a modified version of the default "rapid seq" method. The method was modified by reducing the injection conditions from 1000 V for 22 seconds to 500 V for 11 seconds. Injections were made from deionized water.

EXAMPLE 2

This Example describes experiments indicating that the enzyme binding materials can be added directly to the sequencing reaction prior to thermal cycling. The enzyme binding material can thus remain in the same vessel with the sequencing reaction while the reaction is thermal cycled. The enzyme binding material should be capable of binding a protein, e.g., a polymerase, in the reaction buffer at room temperature, but the enzyme binding material should not interfere with the reaction under the thermal cycling conditions.

A BigDye v.3.1 terminator reaction solution was prepared by combining 80 uL of BigDye Terminator v. 3.1 Ready Reaction Mix (Applied Biosystems) with 10 uL of M13 universal forward sequencing primer (5'-TGTAAAAC-GACGGCCAGT-3'; SEQ ID NO:2) at 3.2 pmol/uL, 15 uL of pGEM (200 ng/uL) plasmid template, and 95 uL of deionized water.

Aliquots of 20 uL of the reaction solution were pipetted into 6 wells of a 96-well PCR tray. Two different types of protein-binding materials were tested as additives to the reaction. Both of the additives described below (100 uL each) were washed five times with 500 uL aliquots of deionized water prior to addition to the reaction solution. After washing, all materials were spun down and left with minimal water above the level of the resin.

The solutions were prepared were as follows. In tubes 1 & 2, 20 uL of reaction solution with no additives was used as a control. In tubes 3 & 4, 20 uL of reaction solution was combined with 1 uL POROS 20 HP2 (Applied Biosystems, Foster City, Calif., USA). In tubes 5 & 6, 20 uL of reaction solution was combined with 1 uL Phenyl Sepharose 6 FF high sub (Amersham Biosciences, Uppsala, Sweden).

The PCR tray was then thermal cycled using the default BigDye cycling conditions on an Applied Biosystems 9700 thermal cycler. Following thermal cycling, the 96 well tray was removed from the thermal cycler and was vortexed for 1 minute. The plate was then spun down in a centrifuge.

Six CentriSep columns were hydrated with 800 uL deionized water, vortexed, and allowed to stand for 2 hours, as per the manufacturer's instructions. Prior to loading the CentriSep columns, the rehydrated columns were centrifuged at 3000 rpm for 2 minutes in a bench top centrifuge. Aliquots of 20 ul of each sequencing reaction solution were pipetted onto a CentriSep column. No special care was taken to avoid pipetting enzyme binding resin along with the sample; in fact some resin was transferred to the CentriSep column. The columns containing samples were centrifuged at 3000 rpm for 2 minutes in a bench top centrifuge. Approximately 20 uL of sample was recovered from each column. An aliquot of 20 uL purified sample was transferred to a 96-well plate for analysis on a DNA sequencer. The samples were analyzed on an ABI 3100 DNA sequencer (Applied Biosystems) using a 36 cm capillary array using POP-6 polymer and the default RapidSeq36 method.

Figure 6:
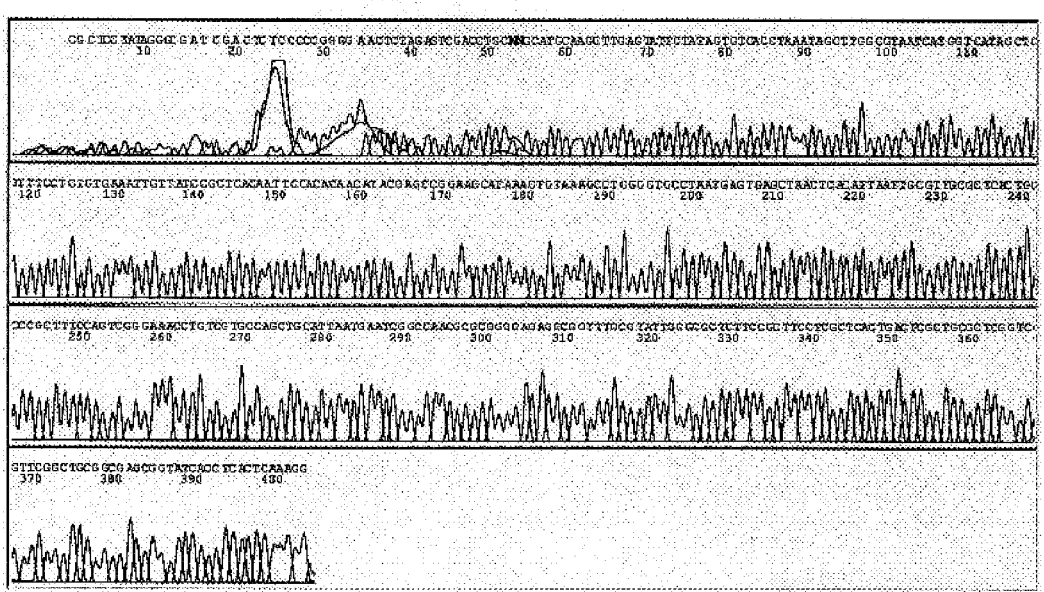
FIG. 6 depicts the results of a sequencing reaction purified with a CentriSep spin column. In this Figure, no protein-binding particles were added to the sequencing reaction during the thermal cycling or after the thermal cycling. The sequence listed in FIG. 6 is SEQ ID NO:11.
Figure 7:
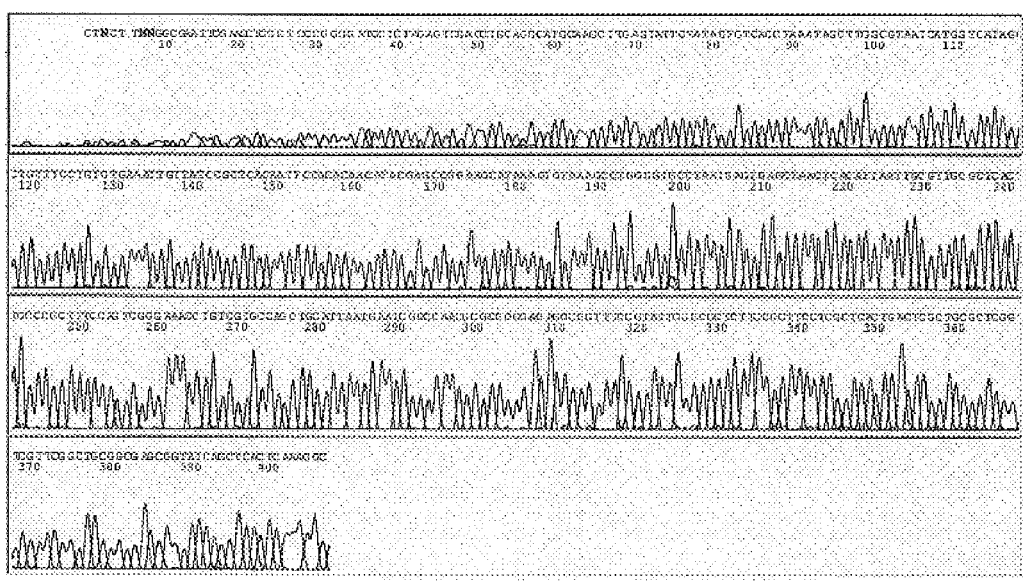
FIG. 7 depicts the results of adding 1 uL of POROS 20 HP2 to a sequencing reaction prior to thermal cycling. The sequence listed in FIG. 7 is SEQ ID NO:12.
Figure 8:
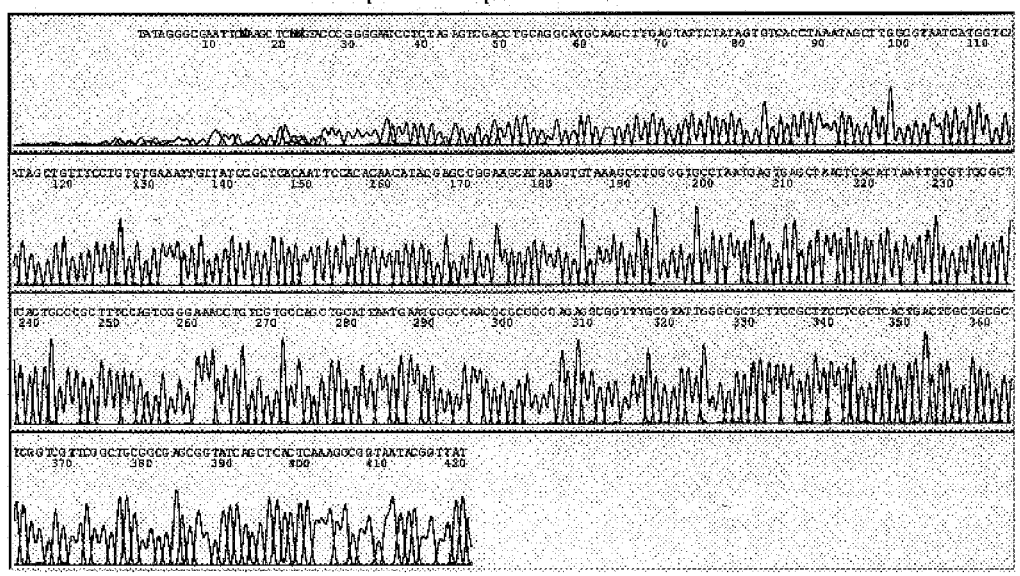
FIG. 8 depicts the results of adding 1 uL of Phenyl Sepharose 6 FF high sub to the sequencing reaction prior to thermal cycling. The sequence listed in FIG. 8 is SEQ ID NO:13.

The results are shown as FIGS. 6-8. Each sample was run in duplicate but only one example of each is shown in the Figures.

FIG. 6 depicts the results when no additive was used in the sequencing reaction and the resulting sequencing reaction was purified using a CentriSep column. Two dye artifacts are visible, which resulted in miscalls of the data between bases 25 and 35.

FIG. 7 depicts results when 1 uL POROS 20 HP2 was added to the sequencing reaction prior to thermal cycling. Note that the enzyme binding material (POROS 20 HP2) remained in the same container as the sequencing reaction while the reaction was thermal cycled. No dye artifacts were observed when the resulting sequencing reaction was purified and analyzed as described previously.

FIG. 8 depicts the results when 1 uL Phenyl Sepharose 6 FF high sub was added to the sequencing reaction prior to thermal cycling. Note that the enzyme binding material (POROS 20 HP2) remained in the same container as the sequencing reaction while the reaction was thermal cycled. No dye artifacts were observed when the resulting sequencing reaction was purified and analyzed as described previously.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All publications, patents and patent applications cited herein are herein incorporated by reference.

DOCUMENTS CITED

U.S. Pat. No. 6,613,525.
U.S. Pat. No. 6,582,987.
U.S. Pat. No. 6,534,269.
U.S. Pat. No. 6,399,304.
U.S. Pat. No. 6,365,350.
U.S. Pat. No. 6,344,326.
U.S. Pat. No. 6,074,827.
U.S. Pat. No. 6,265,193.
U.S. Pat. No. 6,228,628.
U.S. Pat. No. 6,197,555.
U.S. Pat. No. 6,103,537.
U.S. Pat. No. 5,876,934.
U.S. Pat. No. 5,871,929.
U.S. Pat. No. 5,583,162.
U.S. Pat. No. 5,466,591.
U.S. Pat. No. 4,522,953.
U.S. Patent Application Publication Number 20040055956.
U.S. Patent Application Publication Number 20040018559.

U.S. Patent Application Publication Number 20040018116.
U.S. Patent Application Publication Number 20040016702.
U.S. Patent Application Publication Number 20030228706.
U.S. patent application Ser. No. 10/780,963.
Abramson, "Thermostable DNA Polymerases: An Update", In PCR Applications: Protocols for Functional Genomics, Eds. M. A. Innis, D. H. Gelfand, and J. J. Sninsky, Academic Press, 33-47 (1999).
Applied Biosystems Publication Number 4337035.
Frechet et al., in *Polymer*, 20, 675-680 (1979).
Ignatov et al., *FEBS Letters*, 448, 145-148 (1999).
Ignatov et al., *FEBS Letters*, 425, 249-250 (1998).
Kalman et al., "Thermostable DNA Polymerases with Altered Discrimination Properties", Genome Science and Technology, 1, Abstract A-14, P-42 (1995).
McCormick, *Analytical Biochemistry*, 181, 66-74 (1989).
McCormick, U.S. Pat. No. 4,923,978.
Mozdzanowski et. al., *Electrophoresis*, 13, 59-64 (1992).
Reim et. al., *Analytical Biochemistry*, 207, 19-23 (1992).
Richards, *Appl Polym Sci*, 8, 2269-2280 (1964).
Tabor et al., *PNAS*, 92, 6339-6343 (1995).
Yang et. al., *Analytical Biochemistry*, 322, 99-103 (2003).

What is claimed is:

1. A method of reducing dye artifacts from a polynucleotide chain extension reaction, comprising: a) contacting a polynucleotide chain extension reaction solution that comprises protein with at least one protein binding material to form a complex of the protein binding material with the protein; and b) separating the complex from the chain extension reaction solution.

2. The method of claim 1, wherein the protein is an enzyme.

3. The method of claim 2, wherein the enzyme is a DNA polymerase or RNA polymerase.

4. The method of claim 3, wherein the DNA polymerase is a thermostable DNA polymerase.

5. The method of claim 3, wherein the DNA polymerase is a Taq DNA polymerase.

6. The method of claim 5, wherein the mutated Taq DNA polymerase comprises a F667Y mutation.

7. The method of claim 1, wherein the protein is associated with a dye-labeled dideoxynucleotide.

8. The method of claim 1, wherein the chain extension reaction is a DNA sequencing reaction.

9. The method of claim 1, wherein the protein binding material is a membrane.

10. The method of claim 9, wherein the membrane is a porous membrane.

11. The method of claim 10, wherein the porous membrane comprises pores ranging from about 0.01 µm to about 200 µm in size.

12. The method of claim 11, wherein the porous membrane comprises pores ranging from about 0.05 µm to about 100 µm in size.

13. The method of claim 12, wherein the porous membrane comprises pores ranging from about 0.1 µm to about 50 µm in size.

14. The method of claim 10, wherein the porous membrane has a thickness ranging from about 0.1 µm to about 2000 µm.

15. The method of claim 14, wherein the porous membrane has a thickness ranging from about 0.5 µm to about 1500 µm.

16. The method of claim 15, wherein the porous membrane has a thickness ranging from about 0.5 µm to about 1000 µm.

17. The method of claim 1, wherein the protein binding material is a solid support.

18. The method of claim 17, wherein the solid support is a microsphere.

19. The method of claim 18, wherein the microsphere is a polystyrene microsphere.

20. The method of claim 18, wherein the microsphere is a polymer microsphere having a diameter from about 100 nm to about 2000 µm.

21. The method of claim 20, wherein the microsphere has a diameter from about 500 nm to about 1000 µm.

22. The method of claim 20, wherein the microsphere has a diameter from about 1 µm to about 200 µm.

23. The method of claim 18, wherein the microsphere is a nonporous microsphere.

24. The method of claim 18, wherein the microsphere is a microporous microsphere.

25. The method of claim 18, wherein the microsphere is a macroporous microsphere.

26. The method of claim 18, wherein the microsphere has sores with a size greater than about 4000 Angstroms.

27. The method of claim 1, wherein the protein binding material forms a layer on the surface of a solid support.

28. The method of claim 27, wherein the solid support is a porous membrane.

29. The method of claim 27, wherein the protein binding material is associated with the solid support via covalent bonds.

30. The method of claim 1, wherein the protein binding material is mixed with a size-based purification media.

31. The method of claim 1, wherein the protein binding material is layered on a size-exclusion spin column.

32. The method of claim 1, further comprising performing cycle sequencing prior to step (a).

33. The method of claim 1, further comprising purifying the chain extension reaction solution.

34. The method of claim 33, wherein the chain extension reaction solution is purified by size-based purification.

35. The method of claim 34, wherein the chain extension reaction solution is purified by size-based purification using a size-exclusion spin column.

36. The method of claim 34, wherein the chain extension reaction solution is purified by size-based purification using size-excluded ion exchange.

37. The method of claim 1, further comprising analyzing the chain extension reaction solution on a fluorescent DNA sequencer.

38. The method of claim 33, wherein the chain extension reaction solution is contacted with the protein binding material during the purification step.

39. The method of claim 33, wherein the chain extension reaction solution is contacted with the protein binding material prior to the purification step.

40. The method of claim 1, wherein the protein binding material is contacted with the chain extension reaction solution prior to chain extension reaction.

41. The method of claim 40, wherein the protein binding material remains in contact with the chain extension reaction solution during chain extension reaction.

* * * * *